(12) United States Patent
Bädorf

(10) Patent No.: US 6,383,222 B1
(45) Date of Patent: May 7, 2002

(54) KNEE HINGE PROSTHESIS WITH WEAR-RESISTANT DEVICE FOR GUIDING THE PATELLAR COMPONENTS

(75) Inventor: Dirk Bädorf, Frechen (DE)

(73) Assignee: CeramTec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/673,067
(22) PCT Filed: Apr. 16, 1999
(86) PCT No.: PCT/EP99/02757
§ 371 Date: Nov. 30, 2000
§ 102(e) Date: Nov. 30, 2000
(87) PCT Pub. No.: WO99/53870
PCT Pub. Date: Oct. 28, 1999

(30) Foreign Application Priority Data

Apr. 17, 1998 (DE) .......................................... 198 16 984

(51) Int. Cl.[7] .................................................. A61F 2/38
(52) U.S. Cl. .................................. 623/20.21; 623/20.31; 623/20.33
(58) Field of Search ........................... 623/20.21, 20.35, 623/20.27, 20.16, 20.19, 20.31, 20.33

(56) References Cited

U.S. PATENT DOCUMENTS

| 4,355,429 A | | 10/1982 | Mittelmeier et al. |
| 5,021,061 A | * | 6/1991 | Wevers et al. ........... 623/20.21 |
| 5,171,282 A | | 12/1992 | Pequignot |

FOREIGN PATENT DOCUMENTS

| EP | 0 681 815 | 11/1995 |
| WO | WO 95 23567 | 9/1995 |

* cited by examiner

Primary Examiner—Pedro Philogene
(74) Attorney, Agent, or Firm—Fulbright & Jaworski LLP

(57) ABSTRACT

A knee-joint prosthesis comprising a tibial component fixed to the proximal tibia, a femoral component fixed to the distal femur, the femoral component having condylar bearing sections which cooperate in an articulated manner with tibial bearing sections of said tibial component, and an anterior plate section of said femoral component which touches the patella or a patella component fixed to the patella.

6 Claims, 1 Drawing Sheet

KNEE HINGE PROSTHESIS WITH WEAR-RESISTANT DEVICE FOR GUIDING THE PATELLAR COMPONENTS

The invention relates to a knee-joint prosthesis according to the preamble of claim 1.

BACKGROUND OF THE INVENTION

A knee-joint prosthesis having a tibial component, which is fixed to the proximal tibia, and a femoral component, which is fixed to the distal femur and has condylar bearing sections which cooperate in an articulated manner with condylar bearing sections of the tibial component, is known from German Utility Model 89 01 097.3. Apart from this, this knee-joint prosthesis comprises a patellar component, which is fixed to the patella and has a patellar bearing surface which touches an anterior plate section of the femoral component when the prosthetic knee-joint is fully extended. The femoral component with the anterior plate section is a one-piece item made of a metal or a metal alloy such as a cobalt-chromium-molybdenum alloy, titanium or a titanium alloy. The patellar bearing surface is made of a plastic, for example ultra-high molecular weight polyethylene.

Knee-joint prostheses which have no patellar component are also known. In this case, the natural patella, i.e. the bone, touches an anterior plate section of the femoral component directly when the prosthetic knee-joint is fully extended.

A disadvantage of this is that the patellar bearing surface or the natural patella often wears to a great extent, with the result that an exchange operation can become necessary.

SUMMARY OF THE INVENTION

The underlying object of the invention is to improve a knee-joint prosthesis according to the preambles of claims 1 or 3 in such a way that less wear occurs at the patellar bearing surface or the natural patella.

In accordance with the invention, this object is achieved in a first embodiment by the features of claim 1.

Because the anterior plate section and the bearing surface of the patellar component consist of one of the following sliding pairs:
  metallic anterior plate section and metallic bearing surface of the patellar component, or
  ceramic anterior plate section and ceramic bearing surface of the patellar component, or
  ceramic anterior plate section, and bearing surface of the patellar component made of plastics,
a low-wear sliding pair is found, which makes an exchange operation necessary substantially less frequently.

Advantageously, the anterior plate section is constructed as an insert in the femoral component.

In accordance with the invention, the underlying object of the invention is achieved in a second embodiment by the features of claim 3.

Because the anterior plate section is a ceramic insert, the wear is likewise reduced, so that an exchange operation is necessary substantially less frequently. In this embodiment, the knee-joint prosthesis has no patellar component. The natural patella, i.e. the bone, touches the anterior plate section of the femoral component directly.

Advantageously, the ceramic material in all embodiments consists of aluminium oxide, zirconium oxide, mixed ceramic material of aluminium oxide or zirconium oxide, or other biocompatible ceramic materials or coatings.

Further features of the invention are evident from the figures, which are described in the following.

DETAILED DESCRIPTION OF THE INVENTION

Figure 1:
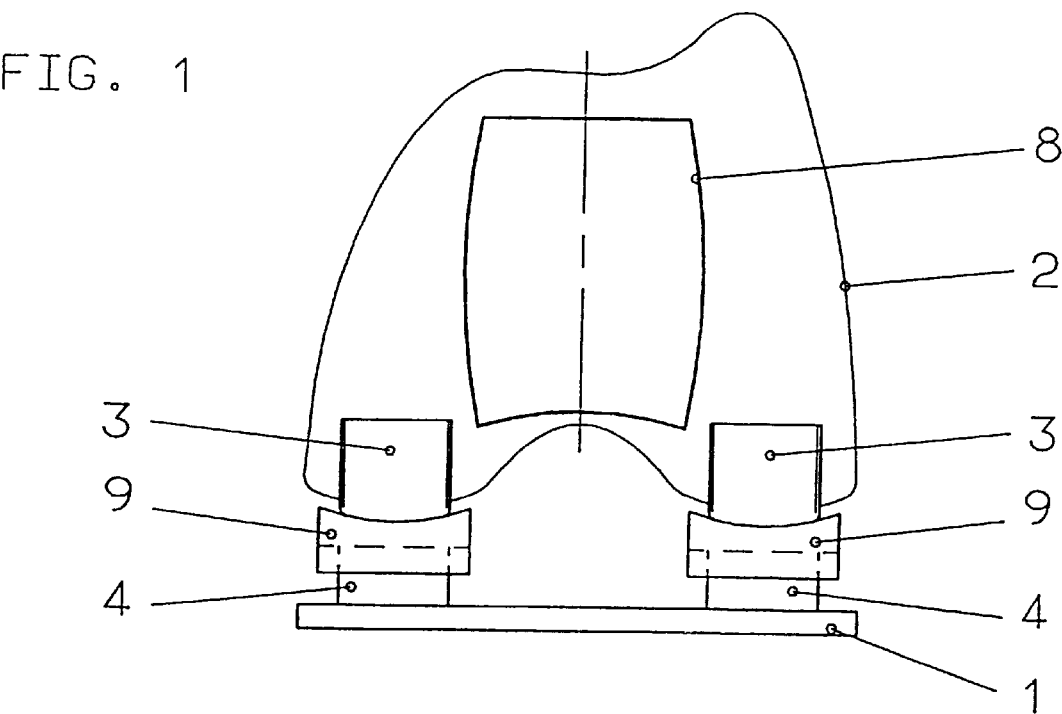
FIG. 1 shows diagrammatically a knee-joint prosthesis having a tibial component, a meniscus and a femoral component.

FIG. 1 shows diagrammatically a knee-joint prosthesis in accordance with the invention having a tibial component 1, which is fixed to the proximal tibia (not shown). This tibial component 1 has tibial bearing sections 4 which cooperate in an articulated manner by way of a meniscus 9 with condylar bearing sections 3 of the femoral component 2. Apart from this, the femoral component 2 has an anterior plate section 8 which in one embodiment cooperates with a patellar bearing surface of a patellar component which is fixed to the patella, and in another embodiment cooperates directly with the patella (6), i.e. the bone, or is used as a sliding surface therefor.

Figure 2:
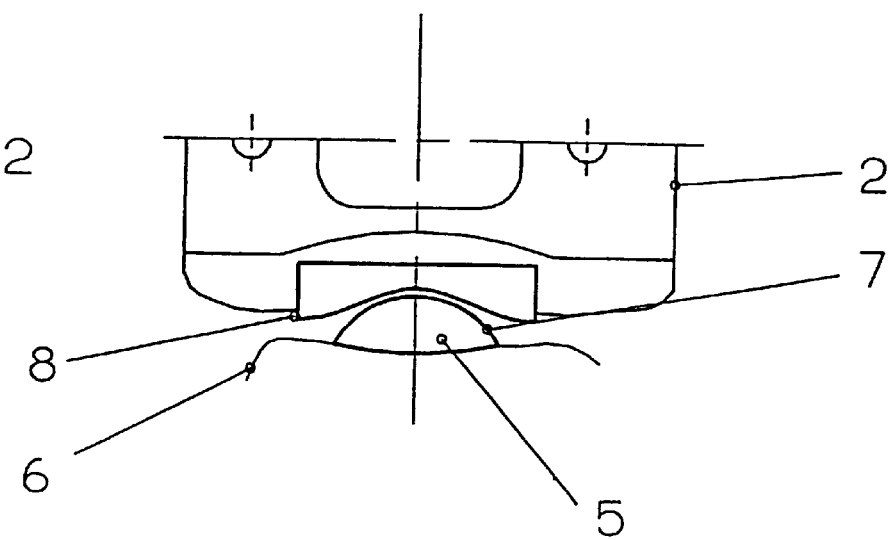
FIG. 2 shows in section the femoral component according to FIG. 1 with adjoining patellar component.

FIG. 2 shows in section the femoral component 2 according to FIG. 1 with adjoining patellar component 5. The patellar component 5 has a bearing surface 7, which slides on the anterior plate section 8.

To reduce wear, in one embodiment the anterior plate section 8 consists of metal and the bearing surface 7 of the patellar component 5 likewise consists of metal.

In another embodiment, the anterior plate section 8 and the bearing surface 7 of the patellar component 5 advantageously consist of ceramic material. Wear in such circumstances is almost excluded. The plate section 8 is advantageously constructed as an insert in the femoral component 2.

In a further preferred embodiment, the anterior plate section 8 consists of ceramic material and the bearing surface 7 of the patellar component 5 consists of plastics, preferably polyethylene. In this case, the plate section 8 is most conveniently constructed as an insert. The fixing of the insert in all embodiments can take place by means of gluing, shrinking, clamping, soldering, welding or other possible types of fixing.

In a further embodiment, the anterior plate section 8 is a ceramic insert and the patella touches the plate section 8 directly.

The ceramic materials used are preferably aluminium oxide, zirconium oxide, mixed ceramic material of aluminium oxide or zirconium oxide, or other biocompatible ceramic materials or coatings.

What is claimed is:

1. A knee-joint prosthesis comprising a tibial component fixed to the proximal tibia, a femoral component fixed to the distal femur, said femoral component further comprising condylar bearing sections which cooperate in an articulated manner with tibial bearing sections of said tibial component, and a patellar component fixed to the patella and comprising a patellar bearing surface which touches an anterior plate section of said femoral component, wherein the anterior plate section and the bearing surface of the patellar component consist of one of the following three sliding pairs:
  (1) a metallic anterior plate section and a metallic bearing surface of the patellar component;
  (2) a ceramic anterior plate section and a ceramic bearing surface of the patellar component;

(3) a ceramic anterior plate section, and bearing a surface of the patellar component made of plastic.

2. A knee-joint prosthesis according to claim 1, wherein the anterior plate section is constructed as an insert in the femoral component.

3. A knee-joint prosthesis according to claim 1, wherein the ceramic material consists of aluminum oxide, zirconium oxide, mixed ceramic material of aluminum oxide or zirconium oxide, or other biocompatible ceramic materials or coatings.

4. A knee-joint prosthesis comprising a tibial component fixed to the proximal tibia, a femoral component fixed to the distal femur, said femoral component further comprising condylar bearing sections which cooperate in an articulated manner with tibial bearing sections of said tibial component, and a natural patella which touches an anterior plate section of said femoral component, wherein said anterior plate section is a ceramic insert.

5. A knee joint prosthesis comprising a tibial component fastened to the proximal tibia and a femoral component fastened to the distal femur, wherein said femoral component is capable of cooperating articulately with joint sections of said tibial component, and wherein an anterior plate section of the femoral component is a ceramic insert capable of contacting a natural patella.

6. A knee joint prosthesis according to claim 5, wherein the ceramic consists of aluminum oxide, zirconium oxide, a mixed ceramic made of aluminum oxide or zirconium oxide or of other bicompatible ceramics or coatings.

* * * * *